United States Patent [19]
Borneman et al.

[11] Patent Number: 5,275,489
[45] Date of Patent: Jan. 4, 1994

[54] APPARATUS AND METHOD FOR INSPECTING AN OPEN-FACE CELL STRUCTURE BONDED TO A SUBSTRATE

[75] Inventors: Karl L. Borneman, Loveland; Douglas A. Jaeger, Cincinnati, both of Ohio; George P. Egan, Union, Ky.

[73] Assignee: General Electric Company, Cincinnati, Ohio

[21] Appl. No.: 963,293

[22] Filed: Oct. 19, 1992

[51] Int. Cl.$^5$ .................... G01N 25/00; G01K 1/14
[52] U.S. Cl. .................... 374/153; 73/150 A; 250/334; 340/600; 374/5; 374/124
[58] Field of Search ............. 374/5, 4, 7, 153, 124; 73/150; 250/334, 330; 340/600

[56] References Cited

U.S. PATENT DOCUMENTS

| | | |
|---|---|---|
| 2,842,957 | 7/1958 | Bacon, Jr. |
| 3,161,038 | 12/1964 | Seltzer et al. |
| 3,427,861 | 2/1969 | Maley |
| 3,566,669 | 3/1971 | Lawrence et al. |
| 3,681,970 | 8/1972 | Wells |
| 3,791,194 | 2/1974 | Pontello |
| 3,860,346 | 1/1975 | Kersch et al. ............ 73/656 X |
| 4,644,162 | 2/1987 | Bantel et al. |
| 4,809,527 | 3/1989 | Mitchell .................. 73/159 X |
| 4,872,762 | 10/1989 | Koshihara et al. ............ 374/5 |
| 4,886,370 | 12/1989 | Koshihara et al. ............ 374/5 |
| 4,988,210 | 10/1989 | Koshihara et al. ............ 374/5 |
| 4,996,426 | 2/1991 | Cielo et al. |
| 5,045,699 | 9/1991 | Schulze et al. ............ 250/330 |
| 5,078,005 | 1/1992 | Krempel et al. |
| 5,111,046 | 5/1992 | Bantel |
| 5,111,048 | 5/1992 | Devitt et al. |

OTHER PUBLICATIONS

"Transient Thermographic NDE of Turbine Blades", X. Maldague, P. Cielo, D. Poussart, D. Craig and R. Bourret, SPIE vol. 1313 Thermosense XII (1990), pp. 157 and 161-171.
"Test of Jet Engine Turbine Blades by Thermography", Kurt Ding, Optical Engineering, Nov./Dec. 1985, vol. 24, No. 6, pp. 1055-1059.
"Test of Jet Engine Turbine Blades by Thermography", Kurt Ding, SPIE vol. 520 Thermosense VII (1984), pp. 52-58.
"Advances in Turbine Blade Temperature Measurements", Frank G. Pollack, Proceedings of the 22nd International Instrumentation Symposium, San Diego, Calif. (May 25-27, 1976), pp. 393/7-397.
Proposed "Thermography and the Development of Advanced Gas Turbine Combustion Systems", G. Myers, J. Van Der Geest and A. Rodrigue, IRIE Seminar 1985, Proceedings of 5th Infrared Information Exchange, New Orleans, La., Oct. 19-31, 1985, Book 2, pp. 23-30.
"Infrared Scanners for Temperature Measurement in Wind Tunnels", Andronicos G. Kantsios, NASA Langley Research Center, Langley, Va., 1976, pp. 149-154.
"Automated Infrared Inspection of Jet Engine Turbine Blades", T. Bantel, D. Bowman, J. Halase, S. Kenue, R. Krisher and T. Sippel, SPIE vol. 581 Thermosense VIII (1986), pp. 18-23.

*Primary Examiner*—Daniel M. Yasich
*Attorney, Agent, or Firm*—Charles L. Moore, Jr.; Jerome C. Squillaro

[57] ABSTRACT

An apparatus and method for inspecting the bonding between a cell structure having a multiplicity of cells which are open at one end and bonded at an opposite end to a substrate are disclosed. The apparatus includes a heater and nozzle arrangement for directing a fluid, such as heated air, having a selected temperature, substantially different from ambient, into the open ends of the cell structure to cause a change in the temperature of the cell structure and radiance therefrom. A sensor is provided for sensing the temperature of the cell structure along the extent thereof or a detector may be provided for detecting the radiance along the cell structure. The temperature sensor or radiance detector generate electrical signals representative of either the temperature sensed or the radiance detected; these electrical signals are electronically converted to an image representative of either the temperatures sensed along the cell structure or the radiance detected from the cell structure to permit detection of any disbonded or plugged cells by differences between either the temperatures sensed or radiance detected along the cell structure. In another embodiment of the present invention, the output of the temperature sensor or radiance detector may be coupled to an alarm to provide a signal if the temperature or radiance varies outside of a predetermined range.

22 Claims, 5 Drawing Sheets

APPARATUS AND METHOD FOR INSPECTING AN OPEN-FACE CELL STRUCTURE BONDED TO A SUBSTRATE

RELATED APPLICATIONS

The present application is related to copending U.S. Pat. Application Ser. No. 07/963,194, filed Oct. 19, 1992, entitled "Method and Apparatus for Inspection of Open Face Honeycomb Structures", by George P. Egan et al., which is assigned to the same assignee as the present invention.

BACKGROUND OF THE INVENTION

The present invention relates to inspection of an open-face cell structure bonded to a substrate and, more particularly, to an apparatus and method for inspecting an open-face honeycomb cell structure of the type commonly used in the aircraft and aerospace industry, including use in gas turbine engines for aircraft propulsion as a seal between non-rotating outer casings and inner rotating components, such as gas turbine engine blades.

Rotating components of a gas turbine engine, such as the fan section, turbine section and compressor section of the engine are typically surrounded by a casing or lining having an interior portion formed of a cell structure having a multiplicity of cells which are typically six sided. These cell structures are commonly referred to as honeycomb because of the distinctive shape of the cells. The interior of each of the hexagonal cells is open and one end of the cell structure is bonded or brazed to a substrate with the open end facing the rotating component of the gas turbine engine.

The honeycomb structure in conjunction with teeth or fingers extending radially from each of the rotating components or blades creates a seal for more efficient operation of the gas turbine engine. The honeycomb structure is abradable to accommodate slight radial growth of the rotating component caused by thermal and centrifugal forces acting upon the rotating component. Thus, the radially extending blade fingers may peel away a minute layer of the honeycomb structure. Therefore, it is important that the honeycomb structure be properly or well bonded to the substrate to prevent a large portion of the honeycomb structure from being peeled from the substrate if the radially extending fingers contact the honeycomb seal which could result in further damage to the engine. Additionally, there should be no leaks between the adjacent honeycomb cells to provide proper sealing and air flow through the engine and therefore efficient engine operation.

Additionally, the honeycomb cells should not be plugged by braze or bonding material because this additional bonding or brazing material within a cell could break off one of the radially extending fingers from a rotating blade resulting in further damage to the engine and also loss of the air seal at this section of the engine resulting in decreased engine efficiency and performance.

Thus, it is important that the honeycomb cell structure be inspected for disbonds between the cell structure and the substrate to which it is bonded or brazed and also for plugged or partially plugged honeycomb cells.

A current inspection apparatus and method for inspecting a honeycomb cell structure is a visual inspection method which includes fixturing the part under an intense light source and viewing each of the individual honeycomb cells through a microscope or similar device for magnifying each of the cells. The operator thus visually determines if a disbond is present or if plugged cells exist. This apparatus and method is dependent upon the skill and vitality of the inspector or operator who must individually observe each of the honeycomb cells. Thus, this method is slow and inefficient and fatigue of the operator can result in inspection errors. While this method may possibly be used to inspect honeycomb cells having diameters of about 1/16" and 1/32", it is impractical for inspecting smaller honeycomb cells as small as about 1/64" in diameter.

Another method for inspecting the honeycomb cell structure involves filling each of the cells with a solvent, such as trichloroethane or the like. The honeycomb component is then rotated with the open face open to the ground. If the cell is properly bonded and sealed to the substrate, the solvent will remain within the cell. If a disbond exists, air will be allowed into the cell through adjacent cells and the solvent will fall out. This method has disadvantages in that plugged cells cannot be detected and honeycomb cells as small as 1/64" in diameter hold the solvent within the cell, even if there is a disbond, because of the surface energy within the smaller cells. Additionally, cleanup of the honeycomb structure after the inspection is necessary and the trichloroethane must be properly handled and disposed of. New environmental standards are also seeking the restrictive use of trichloroethane and similar materials hazardous to the environment which may be utilized with this method.

It is accordingly a primary object of the present invention to provide a novel apparatus and method for inspecting the bonding between a cell structure and a substrate which is not subject to the foregoing disaidvantages.

It is a further object of the present invention to provide an apparatus and method for inspecting the bonding of a cell structure which is reliable, minimizes operator fatigue and operator errors and substantially reduces the inspection time over current inspection methods.

It is a further object of the present invention to provide a novel apparatus and method for inspecting the bonding between a cell structure and a substrate which is environmentally safe.

It is yet another object of the present invention to provide an apparatus and method for inspecting the bonding between a cell structure and a substrate which can be incorporated into an automated system.

These and other objects of the invention, together with the features and advantages thereof, will become apparent from the following detailed specification when read with the accompanying drawings in which like reference numerals refer to like elements.

SUMMARY OF THE INVENTION

In accordance with the present invention, an apparatus for inspecting the bonding between a cell structure having a multiplicity of cells which are each open at one end and bonded to a substrate at an opposite end includes means for directing a fluid, such as heated air, having a selected temperature, substantially different from ambient temperature, into the open ends of the cell structure to cause a change in the temperature of the cell structure and the radiance therefrom. A sensor is provided for sensing the temperature of the cell structure along the extent thereof after the fluid is directed into the open ends or a detector, such as an infrared (IR) camera system or the like, may be provided for detecting the radiance from the cell structure after the fluid is directed into the open ends. The temperature sensor or IR camera generate signals representative of either the temperature sensed or the radiance detected; these signals may be electronically converted by the IR camera system or a plotter mechanism to an image or graph representative of either the radiance along the cell structure or the temperature along the cell structure to permit detection of any disbonded or plugged cells by differences between either the temperatures sensed or the radiance detected along the cell structure. Disbonded cells will be expected to have the highest temperatures compared to plugged cells and properly bonded cells and the IR camera system or plotter mechanism may be preset to represent these cells by a first color in the image. Plugged cells will be expected to have the lowest temperature compared to the disbonded cells and properly bonded cells and the IR camera system or plotter mechanism may be preset to represent these cells by a second color. Properly or well bonded cells will be expected to have temperatures within an intermediate range between the disbonded cells and the plugged cells, and the IR camera system or plotter mechanism may be preset to represent these cells by a third color in the image.

In another embodiment of the present invention, the output of the temperature sensor or radiance detector may be coupled to an alarm to provide a signal if the temperature or radiance varies outside of a predetermined range or the output may be coupled to an X-Y recorder or similar plotting means to provide a graph of the temperature or radiance as the temperature sensor or radiance detector scans along the cell structure.

In a further embodiment of the present invention, the output of the temperature sensor or radiance detector may be coupled to a computer loaded with image processing software to convert the electrical signals from the sensor or detector to video signals for display on a monitor.

In accordance with the present invention, a method for inspecting the bonding between a cell structure having a multiplicity of cells which are each open at one end and bonded at an opposite end to a substrate, includes the steps of: (a) directing a fluid of a selected temperature, substantially different from ambient temperature, into the open ends of a chosen portion of the cell structure to cause a change in irradiance and temperature of the cell structure chosen portion; (b) detecting either the change in irradiance or the change in temperature of the cell structure; (c) converting the detected irradiance or detected temperature to an image representative of either the temperature or irradiance; and (d) detecting any disbonded cells or plugged cells by analyzing the image of the irradiance or temperature.

DETAILED DESCRIPTION OF THE PREFERRED EMBODIMENTS

Figure 1:
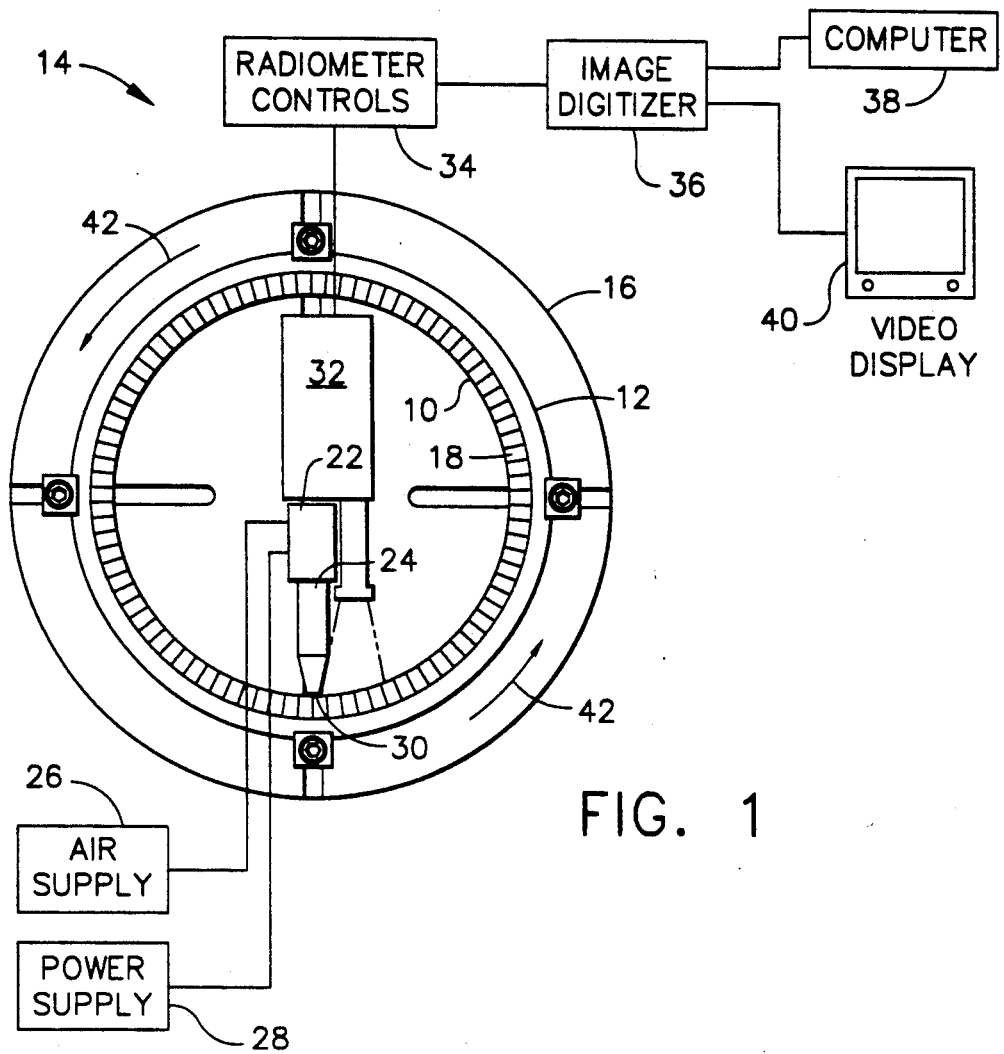
FIG. 1 is a schematic diagram of an apparatus for inspecting the bonding between an open-face cell structure and a substrate in accordance with one embodiment of the present invention.
Figure 2:
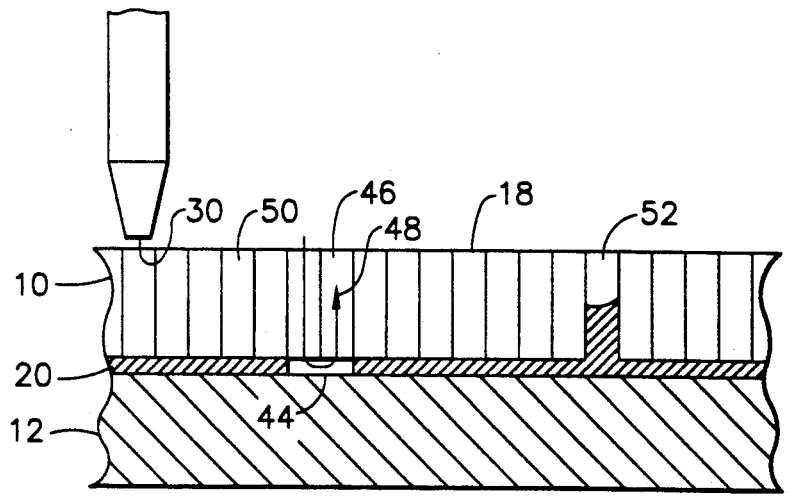
FIG. 2 is a cross sectional view of an open-face cell structure bonded to a substrate illustrating a disbond between the cell structure and the substrate and also illustrating a partially plugged cell.
Figure 3D:
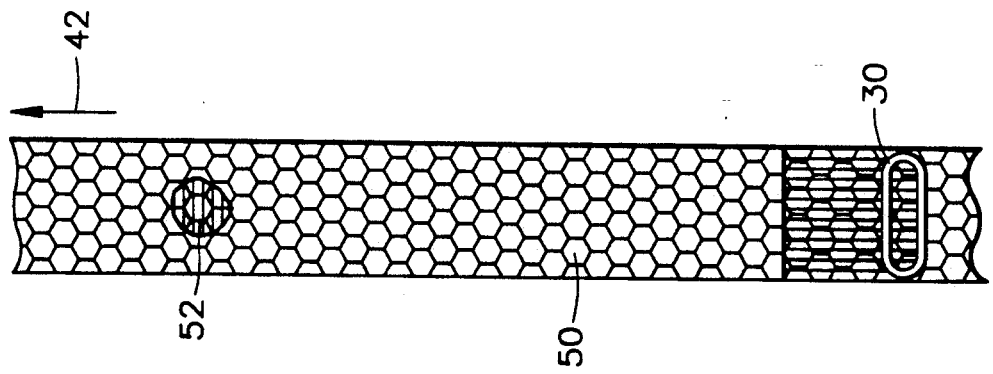
FIGS. 3A-3D illustrate an infrared video image generated by the apparatus of FIG. 1 for detecting disbonds and plugged cells.
Figure 3C:
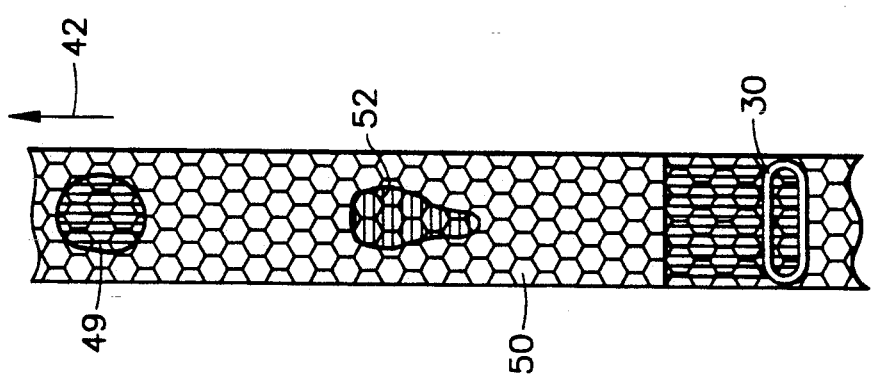
Figure 3B:
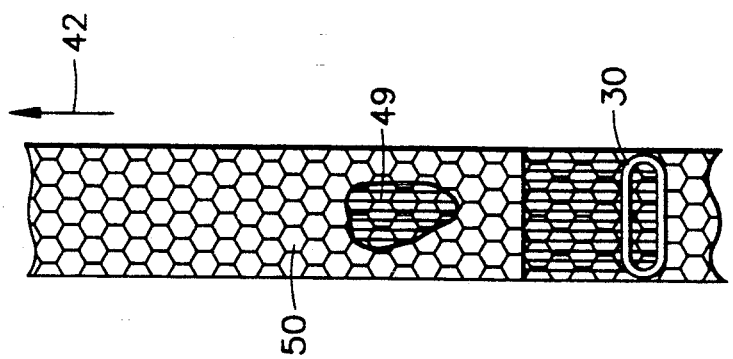
Figure 3A:
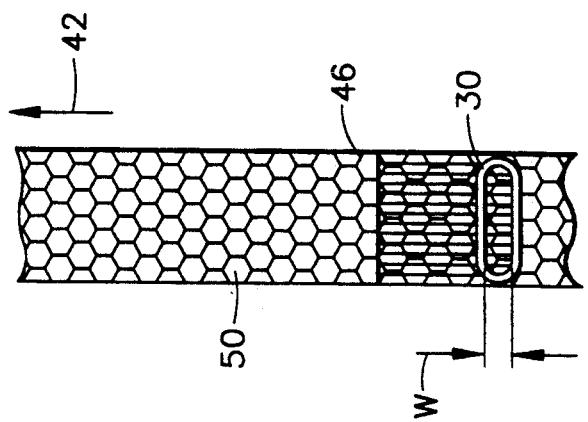

Referring initially to FIG. 1, an apparatus for inspecting the bonding between an open-face cell structure 10 and a substrate 12 to which the cell structure 10 is bonded or brazed is indicated generally at 14, and includes a rotatable fixture arrangement 16 for mounting the cell structure 10 and substrate 12. The cell structure 10 has a multiplicity of individual cells 18 which are each open at one end and bonded or brazed at an opposite end to the substrate 12 by a braze material 20, as best shown in FIG. 2. The present invention will be described for use in inspecting a honeycomb type cell structure for use as a seal in a gas turbine engine; however, those skilled in the art will recognize that the present invention may be used as well to inspect any type of cell structure.

Apparatus 14 further includes a heating mechanism 22 with a nozzle 24 attached thereto for directing heated air at a selected temperature and pressure into the open ends of the cell structure 10. The heating mechanism 22 is attached to a suitable air supply 26 for supplying air to the heating mechanism 22 and is also attached to a power supply 28 for supplying electrical power to heating elements (not shown) in heating mechanism 22 for heating the air before it is directed into the open ends of the cell structure 10 by nozzle 24. The nozzle 24 is preferably a slit-type nozzle having an elongated opening 30 with a width w of about 0.02" and a length to substantially completely cover the width of the cell structure 10, as best shown in FIGS. 3A-3D.

Apparatus 14 further includes an infrared (IR) camera or radiometer 32 and associated radiometer controls 34, such as an Inframetrics 600 IR system or the like. The radiometer controls 34 or infrared camera system may be coupled to an image digitizer 36 for converting the electrical signals to a digital signal for storage or analysis by a computer system 38. The image digitizer may also be coupled to a video display 40 or the radiometer 34 may be directly coupled to the video display 40 for displaying an infrared image of that portion of the cell structure 10 within the field of view of the IR camera 32.

In operation, fixture 16 is rotated by a suitable drive mechanism (not shown), known in the art, to rotate the open end of cell structure 10 relative to the heater nozzle 24 and the field of view of the IR camera 32. The heater nozzle 24 directs heated air at a temperature substantially different than ambient into the open ends of cell structure 10 at a selected pressure of about 30 psi. The temperature may be about 600° F. for a metallic cell structure but would be substantially less for a nonmetallic structure such as composites or the like. The field of view of IR camera 32 is positioned immediately after the nozzle 24 in the direction of rotation of fixture 16 as indicated by arrows 42 in FIG. 1 to capture the infrared image of the heated cell structure 10 immediately after the heated air is directed into the cell structure 10.

Referring also to FIG. 2, if a disbond 44 is present, the air at ambient temperature, which is cooler than the heated air, will quickly escape through an adjacent disbonded cell 46 and be replaced by the heated air as illustrated by arrow 48. The air within the disbonded cells 46 will remain heated momentarily after passing by nozzle 24 and within the field of view of IR camera 32 and will have an IR signature in the infrared image of the cell structure 10 which appears as a hot spot 49 as illustrated in FIGS. 3A-3D because of the higher temperature of the disbonded cells 46. Thus, the disbonded area 44 will have a higher temperature in the image compared to adjacent cells 50 which are well bonded to the substrate 12. The disbonded cells 46 may appear as a particular color, such as red (illustrated by vertical lines or hatching in FIGS. 3A-3D), if the video display 40 is a color monitor or a selected gray scale extreme (black or white), if the video display 40 is monochromatic.

If the bond between the cell structure 10 and the substrate 12 is good, the honeycomb cells are closed at their respective bottom ends and the ambient, cooler air within each of the individual cells 18 is not allowed to quickly escape and be replaced by the heated air from nozzle 24. These well bonded cells 50 will thus have a lower temperature relative to the disbonded cells 46 and will have an IR signature of a particular color, such as white, indicating that they are cooler than the disbonded cells 46 or will have an intermediate gray scale appearance to distinguish them from disbonded or plugged cells as described herein below. Additionally, the heated air rather than being allowed to escape through an adjacent cell, as is the case in the disbonded situation 44, the heat in the well bonded cells 50 will dissipate more readily through the braze 20 and substrate 18 due to heat conduction through these materials which also contributes to the lower IR heat signature of these well bonded cells 50 in the infrared image generated by IR camera 32.

The heat sinking capability of the braze material 20 also permits identification of plugged cells 52 during an inspection operation because the excess braze material in a plugged or partially plugged cell 52 will dissipate the heat more quickly than the well bonded cells 50 and will have a lower temperature than the well bonded cells 50. The plugged cells 50 will, therefore, have an IR signature in the infrared image which appears cooler than the well bonded cells 50 and the disbonded cells 46. The plugged cells 52 will thus appear as the coolest cells in the infrared image and will have a distinctive color such as blue (illustrated by horizontal lines or hatching in FIGS. 3A-3D) in comparison to the hotter, red image of the disbonded cells and the intermediate temperature or the white color of the well bonded cells 50, or the plugged cells may be represented by a gray scale extreme (black or white) opposite to the disbonded cells 46 if a monochromatic video display 40 is used.

While the present invention has been described with respect to directing heated air into the open ends of the cell structure 10, those skilled in the art will recognize that chilled air at a substantially cooler temperature than the ambient air in the cell structure 10 could be used as well with the color indications for the disbonded and plugged cells being reversed from those of the infrared image when heated air is directed into the open ends of the cell structure 10.

Figure 4A:
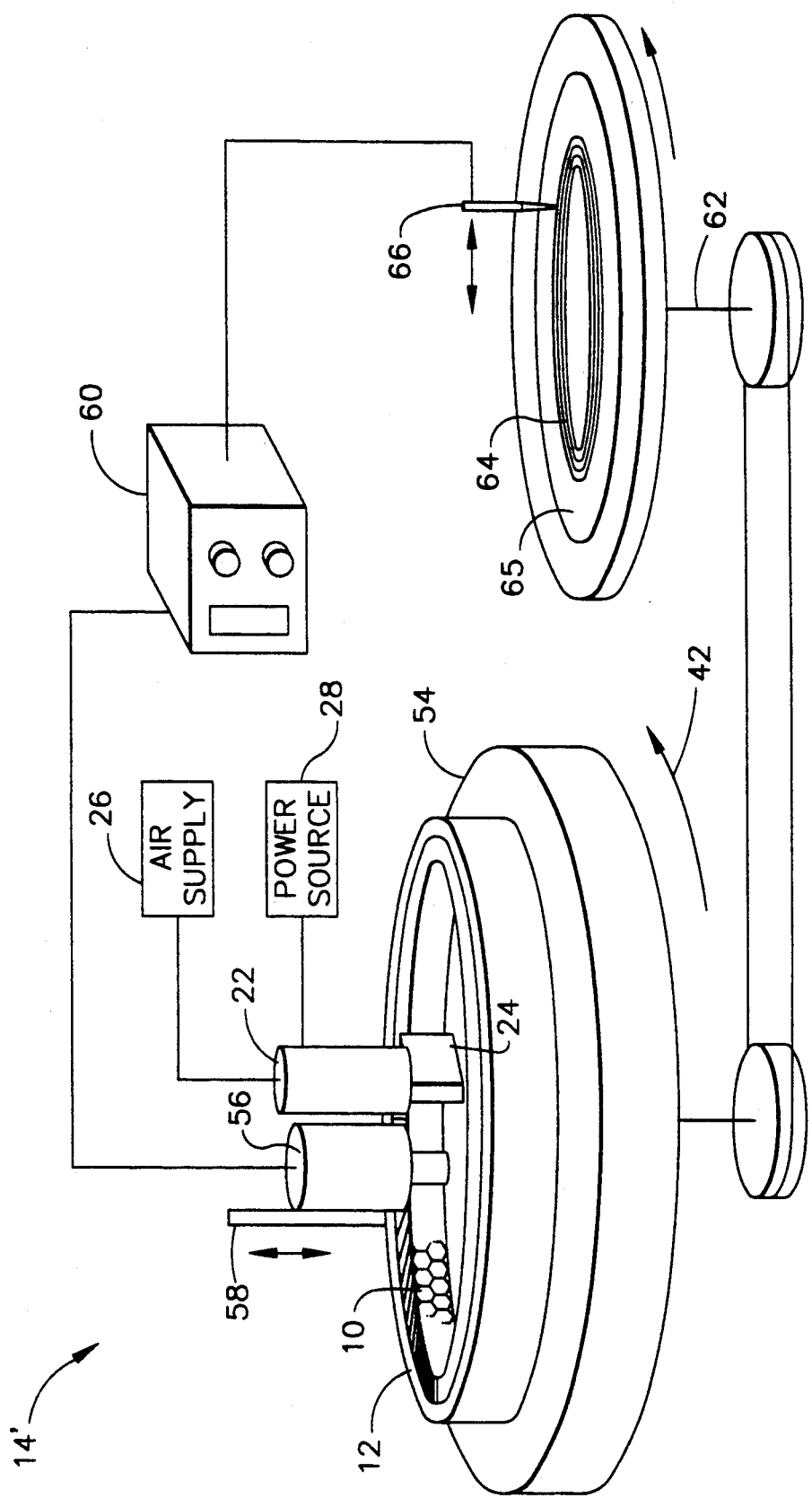
FIG. 4A is a schematic diagram of an apparatus for inspecting the bonding between an open-face cell structure and a substrate in accordance with another embodiment of the present invention.

Another embodiment of the present invention, which is less expensive to implement than the embodiment shown in FIG. 1, is shown in FIG. 4A. The inspection apparatus 14' includes a fixture and rotating table combination 54 for mounting and holding the cell structure 10 in position during an inspection operation. The apparatus 14' further includes a single point temperature sensor or a multipoint scanning thermometer or temperature sensor 56, such as a Raytek ® Thermalet ® MP-4 multipoint scanning thermometer or the like. If a single point thermometer or temperature sensor 56 is used then sensor 56 may be mounted to an axis 58 for indexing the point sensor 56 across the width of the cell structure 10. Sensor 56 is positioned to detect or sense the temperature immediately behind the heater nozzle 24 in the direction of motion 42 of the cell structure 10 when turntable 54 is being rotated. Sensor 56 is coupled to a gray-scale pen amplifier 60 and plotter mechanism 62 as illustrated schematically in FIG. 4A. The plotter mechanism 62 is coupled either mechanically or electrically to rotating table 54 so that both turn in coordination with one another to provide a thermograph or polar plot 64 of the temperatures sensed along the cell structure 10, as it is rotated past heater nozzle 24 and temperature sensor 56, and to permit location of the disbonded or plugged cells in the cell structure 10. If a single point temperature sensor 56 is used, after a complete rotation of cell structure 10, sensor 56 is indexed to a new position and pen 66 of plotter mechanism 62 will be indexed in association therewith to record the temperatures sensed during another revolution of the cell structure 10 at this new indexed position. This indexing and rotation cycle will be repeated until substantially the entire width of the cell structure 10 has been inspected. If a multipoint scanning thermometer is used for sensor 56, depending upon the width of scan of the scanning thermometer, only a single revolution of cell structure 10 may be required to obtain a thermograph or polar plot 64 of the open end of the cell structure 10.

Figure 5:
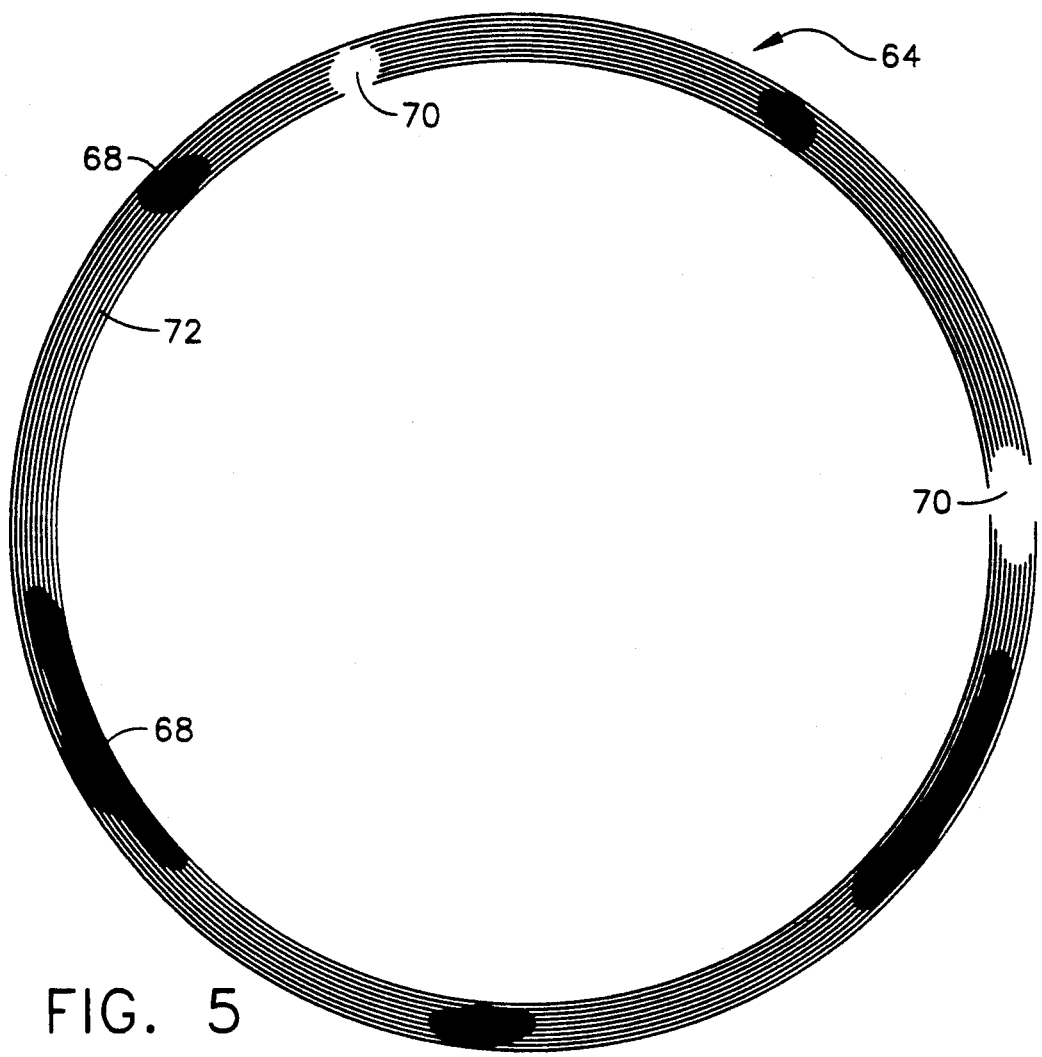
FIG. 5 is an illustration of an image or thermograph generated by the apparatus of FIG. 4 for detecting disbonds and plugged cells.

In operation, the heater nozzle 24 directs heated air having a selected temperature substantially different from ambient into the open ends of the cell structure 10 at a selected pressure of about 30 psi to cause an increase in temperature in the cell structure. The sensor 56 positioned immediately behind the heater nozzle 24 senses the temperature, either at a point or across the width of the cell structure 10, if a multipoint scanning thermometer is used for sensor 56, and converts the temperatures sensed to electrical signals. The gray scale pen amplifier 60 receives the electrical signals from the sensor 56 and causes pen 66 to generate an image or polar plot 64 on thermally sensitive paper 65 which is representative of the sensed temperatures across the open face of cell structure 14. An example of such an image or polar plot 64 is illustrated in FIG. 5. A disbonded cell is represented in the thermograph of FIG. 5 by a black area 68 and the plugged cells are represented by a white area 70 relative to the intermediate gray scale areas 72 representing the well bonded or properly bonded cells 50.

Figure 4B:
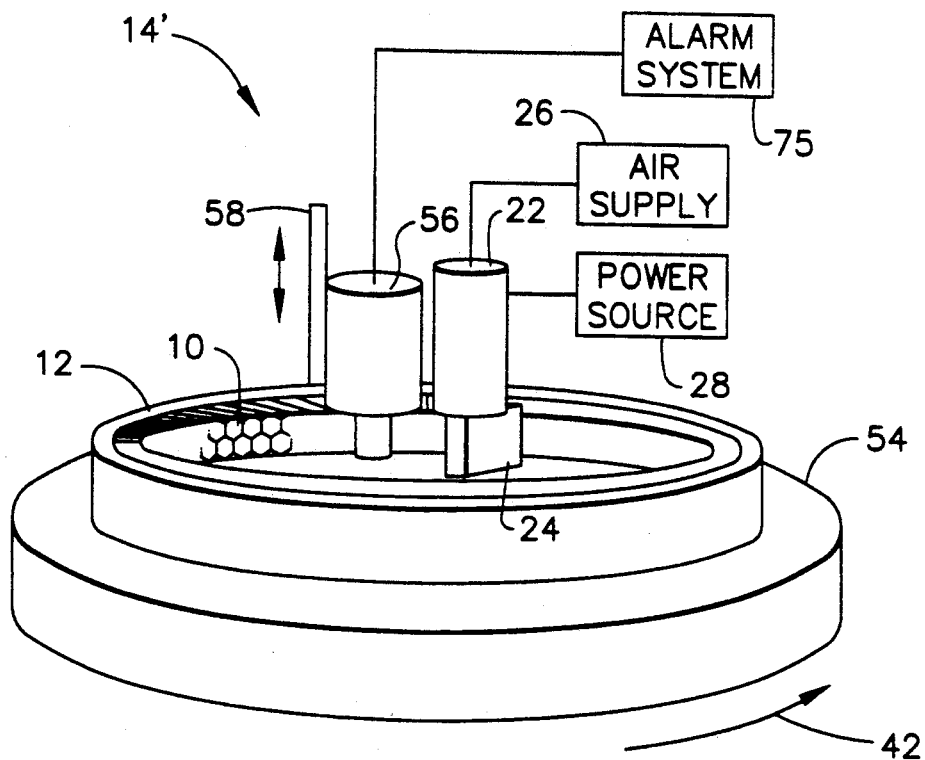
FIG. 4B is a schematic diagram of an apparatus for inspecting the bonding between an open-face cell structure and a substrate in accordance with a further embodiment of the present invention.
Figure 7:
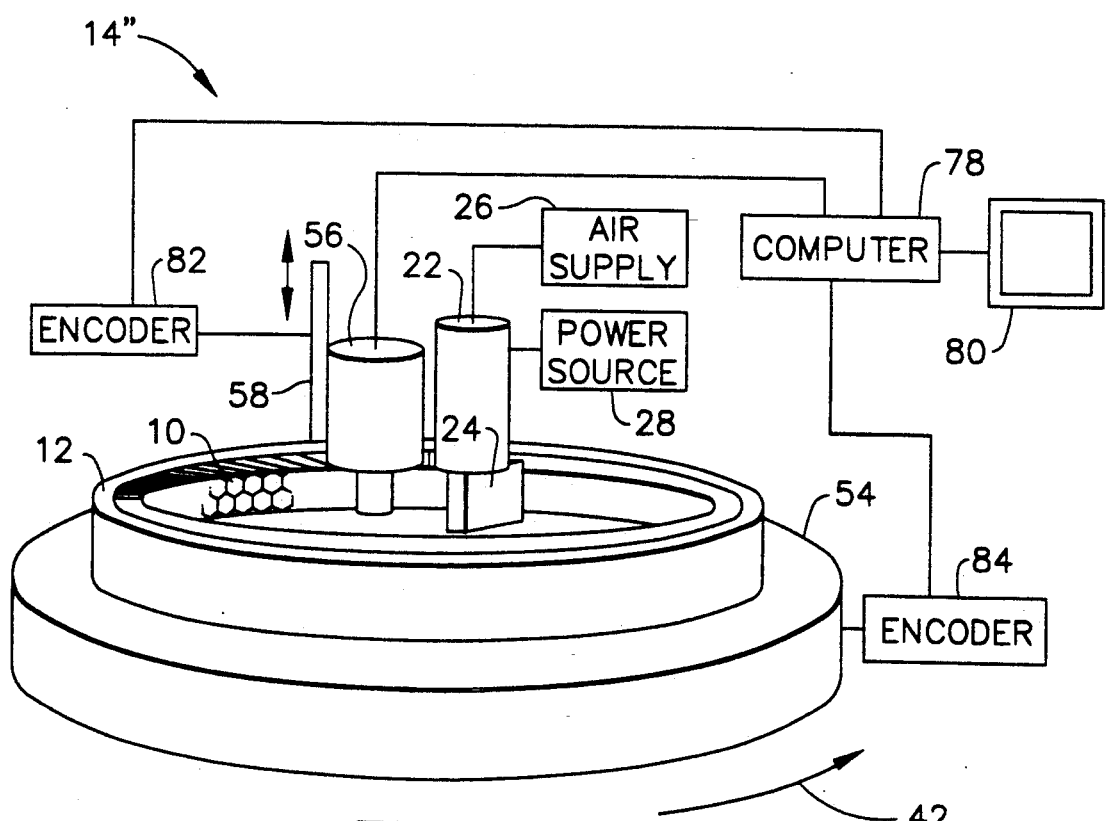
FIG. 7 is a schematic diagram of an apparatus for inspecting the bonding between an open-face cell structure and a substrate in accordance with a further embodiment of the present invention.
Figure 6:
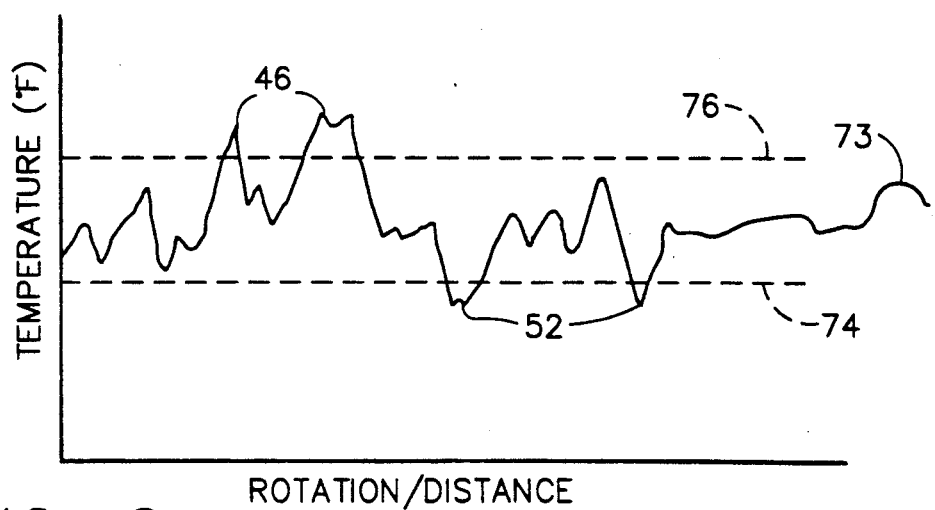
FIG. 6 is an illustration of a graph of temperature v. rotation or distance along the open-face structure which may be provided by the present invention.

In an alternate embodiment of the present invention, gray scale pen amplifier 60 and plotter mechanism 62 may be replaced by an XY recorder which is coupled to the output of the temperature sensor 56 to provide a linear plot or graph 73 as shown in FIG. 6. All those temperature values above a selected range of temperature values indicated by broken lines 74 and 76 would correspond to disbonded cells 46 and all of those temperatures below the predetermined range 74 of temperatures would represent plugged cells 52. Those skilled in the art will also recognize that the output of temperature sensor 56 could equally be coupled to an alarm system is, as shown in FIG. 4B, to merely provide an indication when the temperature sensed swings outside of the predetermined range 74 and 76 of temperatures to permit an accept or reject decision with respect to the cell structure 10 under inspection.

In a more sophisticated embodiment of the present invention, the output of temperature sensor 56 may be connected to the input of a computer system 78 which may be loaded with image processing software, such as PV~WAVE TM as made by Precision Visuals®, Inc. of Boulder, Colorado, or the like, to convert the electrical signals representative of the temperature sensed by temperature sensor 56 to a video image for display on monitor 80. Additionally, computer system 78 may store historical and statistical data from the inspection of other cell structures 10 for comparison and analysis to permit tracking of trends and to permit correction or improvement of the brazing process for bonding the cell structure 10 to the substrate 18 with little or no disbonds 44 or plugged cells 52 (FIG. 2). The inspection apparatus 14" may include encoders 82 and 84 to provide precise information as to the location of any disbonded cells 46 or plugged cells 52.

While the present invention has been described with respect to the inspection of a honeycomb cell structure for use as part of a seal for a gas turbine engine, those skilled in the art will recognize that the principles, techniques and apparatus of the present invention may be applied as well to similar structures and that the present invention is not limited to the specific embodiments described and illustrated herein. Different embodiments and adaptations besides those shown herein and described, as well as many variations, modifications and equivalent arrangements will now be apparent or will be reasonably suggested by the foregoing specification and drawings, without departing from the substance or scope of the invention. While the present invention has been described herein in detail in addition to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. An apparatus for inspecting the bonding between a cell structure having a multiplicity of cells which are each open at one end and bonded at an opposite end to a substrate, comprising;

means for directing a fluid having a selected temperature, substantially different from ambient, into the open ends of the cell structure at a selected pressure to cause a change in temperature of the cell structure and radiance therefrom;

means for detecting the radiance from the cell structure;

means for generating an image representative of the radiance from the cell structure to detect any disbond or a plugged cell, a disbond between a cell and the substrate having a higher temperature than a cell which is properly bonded to the substrate, and a plugged cell having a lower temperature than a properly bonded cell; and means for moving one of said cell structure, and said fluid directing means and said detecting means relative to one another to inspect the cell structure.

2. The apparatus of claim 1, wherein said detecting means and said image generating means are an infrared imaging radiometer coupled to a video display.

3. The apparatus of claim 1, wherein said fluid is air heated to a temperature substantially above ambient.

4. The apparatus of claim 1, wherein said cell structure is a honeycomb ring seal structure for use in a gas turbine engine, and said moving means comprises a rotatable fixture for mounting the honeycomb ring structure for rotation relative to said fluid directing means and said radiance detecting means, said honeycomb ring structure being rotated to cause said fluid to be directed into the open ends of the honeycomb seal immediately before said radiance detecting means.

5. An apparatus for inspecting the bonding between a cell structure having a multiplicity of cells which are each open at one end and bonded at an opposite end to a substrate, comprising:

means for directing a heated gas having a selected temperature into the open ends of a selected portion of the cell structure to cause an increase in temperature in the cell structure;

means for sensing the temperature across the selected portion of the cell structure at the open ends thereof;

means for generating an image representative of the sensed temperature across the selected portion to detect any disbond or a plugged cell, a disbonded cell having a higher temperature than a cell which is properly bonded to the substrate, and a plugged cell having a lower temperature than a cell which is properly bonded to the substrate; and means for moving one of said cell structure, and said fluid directing means and said detecting means relative to one another to scan across the cell structure.

6. The apparatus of claim 5, wherein said image is a graph of temperature plotted against position along the selected portion, all temperatures above a predetermined range indicating a disbond and all temperatures below said predetermined range corresponding to a plugged cell, wherein said predetermined range corresponds substantially to a properly bonded cell.

7. The apparatus of claim 5, wherein said temperature sensing means is a multipoint scanning thermometer which generates electrical signals representative of the temperatures sensed.

8. The apparatus of claim 7, wherein said image generating means is a gray scale pen amplifier and plotter mechanism coupled to said multipoint scanning thermometer to receive said electrical signals and to generate said image representative of the sensed temperatures, disbonded cells being represented by a chosen gray scale color extreme, plugged cells being represented by an opposite gray scale color extreme and properly bonded cells being represented by an intermediate gray scale color.

9. The apparatus of claim 7, wherein said image generating means comprises electronic image processing means for converting said electrical signals to video signal for display on a video monitor to permit distinction between disbonded cells, plugged cells and properly bonded cells.

10. The apparatus of claim 5, wherein said temperature sensing means is positioned after said heated gas directing means relative to a direction of motion of one of the cell structure, and said gas directing means and said detecting means.

11. The apparatus of claim 5, wherein said cell structure is a honeycomb ring seal structure for use in a gas turbine engine, and said moving means comprises a rotatable fixture for mounting the honeycomb ring structure for rotation relative to said heated gas directing means and said temperature sensing means, said honeycomb ring structure being rotated to cause said heated gas to be directed into the open ends of the honeycomb seal immediately before said temperature sensing means.

12. The apparatus of claim 11, wherein said heated gas directing means comprises a slit-type nozzle having an elongated opening with a width of about 0.02" and a length to substantially completely cover the width of the honeycomb ring.

13. The apparatus of claim 5, wherein said temperature sensing means is a signal point temperature sensor which generates electrical signals representative of the temperature sensed.

14. The apparatus of claim 13, further comprising
means for indexing said single point temperature sensor across a width of the cell structure; and
wherein said image generating means is a gray-scale pen amplifier and plotter mechanism coupled to said single point temperature sensor to receive said electrical signals and to generate said image representative to the sensed temperatures, disbonded cells being represented by a chosen gray scale color extreme, plugged cells being represented by an opposite gray scale color extreme and properly bonded cells being represented by an intermediate gray scale color.

15. An apparatus for inspecting the bonding between a cell structure having a multiplicity of cells which are each open at one end and bonded at an opposite end to a substrate, comprising:
means for directing a fluid having a selected temperature, substantially different from ambient, into the open ends of the cell structure to cause a change in temperature of the cell structure;
means for sensing the temperature of the cell structure at the open ends thereof;
means for generating an alarm signal in response to the temperature of the cell structure varying outside of a predetermined range; and
means for moving one of the cell structure, and said fluid directing means and said detecting means relative to one another.

16. A method for inspecting the bonding between a cell structure having a multiplicity of cells which are each open at one end and bonded at an opposite end to a substrate, comprising the steps of:

(a) directing a fluid of a selected temperature, substantially different from ambient temperature, into the open end of a chosen portion of the cell structure to cause a change in irradiance and temperature of the cell structure chosen portion;

(b) detecting at least one of the change in irradiance from the cell structure and temperature of the cell structure;

(c) generating an image representative of one of the irradiance and the temperature of the cell structure;

(d) detecting a higher temperature relative to a properly bonded cell created by any disbonded cells and a lower temperature relative to a properly bonded cell created by any plugged cells by analyzing the image; and (e) moving one of the cell structure, and a fluid directing means and a detecting means relative to one another to inspect the bonding of the cell structure.

17. The method of claim 16, wherein step (c) comprises the step of generating a thermograph of the temperature of the cell structure chosen portion, a disbonded cell being represented by a chosen gray scale color extreme, a plugged cell being represented by an opposite gray scale color extreme and a properly bonded cell being represented by an intermediate gray scale color.

18. The method of claim 16, wherein a disbonded cell is represented by a first color in said image, a plugged cell is represented by a second color and a well bonded cell is represented by a third color in said image.

19. The method of claim 16, wherein step (a) comprises the step of forcing air at a temperature substantially above ambient into the open end of the chosen cell portion.

20. The method of claim 16, wherein step (b) comprises the step of focusing an infrared radiation detection device on the chosen cell structure portion to provide at least one infrared image of the radiance from the chosen portion caused by the fluid.

21. The method of claim 16, wherein step (b) comprises the step of scanning a temperature sensing probe across the cell structure chosen portion to generate electrical signals representative of the detected temperatures and step (c) comprises the step of generating an image corresponding to the electrical signals, a disbond being represented by a first color, a plugged cell being represented by a second color and a properly bonded cell being represented by a third color.

22. An apparatus for inspecting the bonding between a cell structure having a multiplicity of cells which are each open at one end and bonded at an opposite end to a substrate, comprising:
means for directing a fluid having a selected temperature, substantially different from ambient, into the open ends of the cell structure to cause a change in radiance from the cell structure;
means for sensing the radiance from the cell structure;
means for generating an alarm signal in response to the radiance varying outside of a predetermined range; and
means for moving one of said cell structure, and said fluid directing means and said detecting means relative to one another.

* * * * *